(12) United States Patent
Shen et al.

(10) Patent No.: US 9,714,916 B2
(45) Date of Patent: Jul. 25, 2017

(54) PARTICLE ANALYZERS AND PARTICLE TEST CONTROL METHODS AND DEVICES THEREOF

(71) Applicant: Shenzhen Mindray Bio-Medical Electronics Co., Ltd., Shenzhen (CN)

(72) Inventors: Tao Shen, Shenzhen (CN); Huilin Shi, Shenzhen (CN); Jin Teng, Shenzhen (CN); Wenheng Guo, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 14/355,547

(22) PCT Filed: Oct. 25, 2012

(86) PCT No.: PCT/CN2012/083512
§ 371 (c)(1),
(2) Date: Aug. 8, 2014

(87) PCT Pub. No.: WO2013/064033
PCT Pub. Date: May 10, 2013

(65) Prior Publication Data
US 2014/0339101 A1 Nov. 20, 2014

(30) Foreign Application Priority Data
Oct. 31, 2011 (CN) .......................... 2011 1 0338176

(51) Int. Cl.
*G01N 15/12* (2006.01)
*G01N 27/416* (2006.01)

(52) U.S. Cl.
CPC ......... *G01N 27/4163* (2013.01); *G01N 15/12* (2013.01); *G01N 2015/1272* (2013.01); *G01N 2015/1281* (2013.01)

(58) Field of Classification Search
CPC ........................ G01N 15/12; G01N 2015/1281
See application file for complete search history.

(56) References Cited

U.S. PATENT DOCUMENTS

| 4,165,484 A * | 8/1979 | Haynes .............. G01N 15/1227 324/71.4 |
| 6,909,269 B2 | 6/2005 | Nagai et al. |
| 8,146,407 B2 * | 4/2012 | Atchley ............. G01N 15/1209 73/61.71 |

FOREIGN PATENT DOCUMENTS

| CN | 101173887 A | 5/2008 |
| CN | 101750477 A | 6/2010 |

* cited by examiner

*Primary Examiner* — Paul Hyun
(74) *Attorney, Agent, or Firm* — Kory D. Christensen; Polsinelli LLP (57) ABSTRACT

The present disclosure provides a particle analyzer and a particle test control method and device thereof. The method comprises: after acquiring a diluted sample, preserving a part of the diluted sample, and monitoring whether a pore blocking event occurs during a counting process; when the pore blocking event occurs, suspending the test of the sample, and performing an unblocking operation; and after the unblocking operation is completed, controlling a liquid addition system to again acquire the preserved part of the sample from a reaction cell or a tube of the liquid addition system and inject it into a counting cell, and then re-counting the sample in the counting cell by an impedance method. The method makes full use of the residual diluted sample for a second test to eliminate the impact of pore blocking that occurs in the first measurement of the sample on the test result, and there is no need to be place the sample tube again at test position for re-acquisition and re-dilution, thereby reducing the probability of pore blocking.

13 Claims, 10 Drawing Sheets

PARTICLE ANALYZERS AND PARTICLE TEST CONTROL METHODS AND DEVICES THEREOF

RELATED APPLICATION

This application claims priority to Chinese Patent Application No. 201110338176.4, filed on Oct. 31, 2011, the disclosure of which is fully incorporated herein by reference.

TECHNICAL FIELD

The present disclosure relates to the field of biochemical analysis, more particularly to particle analyzers and particle test control methods and devices thereof.

BRIEF SUMMARY

The present disclosure relates to particle analyzers and particle test control methods and devices thereof that may reduce probability of pore blocking.

In one aspect of the present disclosure, a particle test control method is provided that can include:
 controlling a sample acquisition system to acquire a sample in a test location;
 injecting the acquired sample into a reaction cell to obtain a diluted sample;
 controlling a liquid addition system to acquire the diluted sample from the reaction cell and inject the acquired diluted sample into a counting cell, and keeping a liquid discharge valve of the reaction cell in a close status to maintain a residual diluted sample in the reaction cell;
 counting the sample in the counting cell by impedance method, and monitoring whether a pore blocking event occurs during the counting;
 suspending a next sample test and performing an unblocking operation when a pore blocking event occurs; and
 controlling the liquid addition system to acquire the diluted sample again from the reaction cell and inject the acquired diluted sample into the counting cell after the unblocking operation, and re-counting the sample in the counting cell by impedance method.

In another aspect of the present disclosure, a particle test control device used in a particle analyzer is provided that can include:
 a first control unit, which controls a liquid addition system to acquire a diluted sample from a reaction cell and inject the acquired diluted sample into a counting cell;
 a second control unit, which couples to the first control unit and controls a liquid discharge valve of the reaction cell to be in a close status so as to maintain a residual diluted sample in the reaction cell after the first control unit controls the liquid addition system to acquire the diluted sample from the reaction cell;
 a third control unit, which couples to the first control unit and controls counting of the sample of the counting cell by impedance method after the sample is injected into the counting cell;
 a pore blocking monitoring unit, which receives outputted pore voltage during the counting process by impedance method, determines whether pore blocking occurs, and outputs a pore blocking event when pore blocking occurs; and
 a fourth control unit, which couples to the pore blocking monitoring unit, and suspends a test and performs an unblocking operation, outputs a control signal to the first control unit after the unblocking operation so that the first control unit controls the liquid addition system to acquire the diluted sample again from the reaction cell and inject the acquired diluted sample into the counting cell.

In still another aspect of the present disclosure, a particle analyzer is provided that can include:
 a reaction cell, where a sample is diluted, the reaction cell including a liquid inlet tube, a liquid outlet tube and a liquid discharge tube, the liquid discharge tube having a liquid discharge valve which can switch between a close status and an open status based on a control signal;
 a counting system, which including a counting cell, the counting system counts the sample injected into the counting cell by impedance method and output a pore voltage;
 a liquid addition system, which can acquire the diluted sample from the reaction cell and inject the acquired diluted sample into the counting cell; and
 a signal processing and control apparatus, which
  receives the pore voltage, and shapes and recognizes signals;
  is configured to control the liquid discharge valve of the reaction cell to be close status so as to maintain a residual diluted sample in the reaction cell after the liquid addition system acquires the diluted sample from the reaction cell and inject the acquired diluted sample into the counting cell;
  monitors pore blocking based on the pore voltage during the counting, suspends a next sample test and performs an unblocking operation when the pore blocking occurs, and;
  controls the liquid addition system to acquire and inject the diluted sample to the counting cell again after the unblocking operation, and re-counting the sample of the counting cell by impedance method.

In yet another aspect of the present disclosure, a particle test control method of a particle analyzer is provided that can include:
 controlling a sample acquisition system to acquire a sample in a test location;
 injecting the sample into a plurality of reaction cells to perform multistage dilution, until a diluted sample having a satisfactory dilution ratio is obtained in the last reaction cell;
 controlling a liquid addition system to acquire the diluted sample from the last reaction cell and inject the acquired diluted sample into a counting cell, and keeping a liquid discharge valve of at least one of the reaction cells in a close status to maintain a residual diluted sample in the reaction cell;
 counting the sample of the counting cell by impedance method, and monitoring whether a pore blocking event occurs during the counting;
 suspending a sample test and performing an unblocking operation when a pore blocking event occurs;
 obtaining a diluted sample having the satisfactory dilution ratio from a reaction cell having the residual diluted sample; and
 injecting the diluted sample having the satisfactory dilution ratio into the counting cell again, and re-counting the sample in the counting cell by impedance method.

In yet another aspect of the present disclosure, a particle test control method of a particle analyzer is provided that can include:
 controlling a sample acquisition system to acquire a sample in a test location;

injecting the sample into a reaction cell to obtain a diluted sample;

controlling a liquid addition system to acquire the diluted sample from the reaction cell, inject part of the diluted sample to a counting cell and keep a residual diluted sample in the liquid addition system;

counting the sample of the counting cell by impedance method, and monitoring whether a pore blocking event occurs during the counting;

suspending a sample test and performing an unblocking operation when a pore blocking event occurs; and controlling the liquid addition system to inject the residual diluted sample into the counting cell after the unblocking operation, and re-counting the sample of the counting cell by impedance method.

DETAILED DESCRIPTION

A particle analyzer may be used in medical or biochemical study such as biochemical analysis, which can classify and count particles of a mixture. A blood cell analyzer is a common particle analyzer. A blood cell analyzer can count and classify human blood cells, whose measurement method may include: adding a certain amount of blood sample to a certain amount of diluent that can keep cell morphology and have conductive property; the mixture is pushed through a pore by a driving source. The equivalent impedance of the pore may increase when a cell passes the pore because the cell can be less conductive. Under constant current condition, voltage may change with the impedance proportionally, i.e. voltage waveform may reflect the impedance change while the cell passes through the pore. A voltage pulse can be obtained when a cell passes through a pore, where the pulse height indicates volume size of the cell. So cells can be classified depending on their height of voltage pulse, this method is called impedance method.

Figure 1:
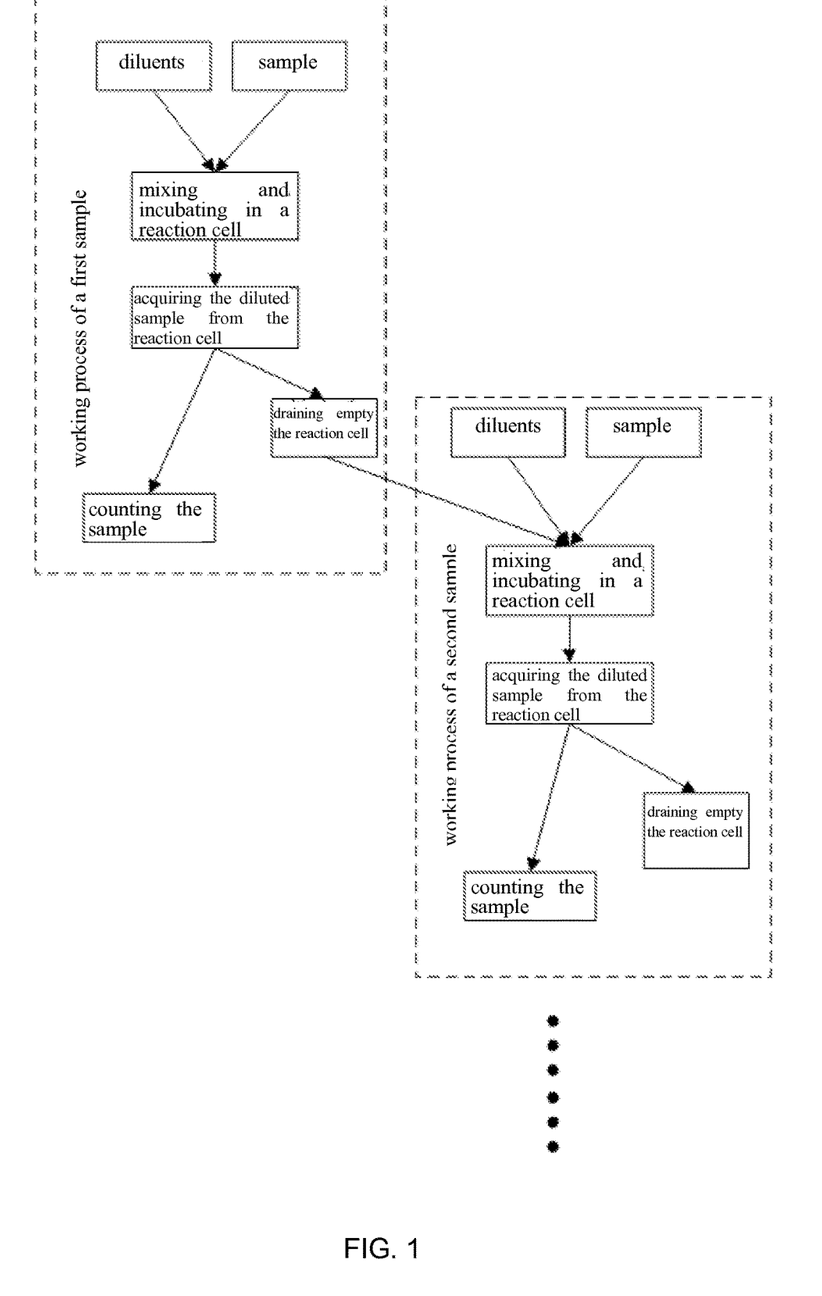
FIG. 1 is a test time sequence diagram of a blood cell analyzer in accordance with an embodiment of the present disclosure.

The pore used in the measurement is a precision element, where the pore size is between 50-120 μm. Due to the small size of the pore, the pore can be easily blocked by proteins, cell debris, blood clot, lipids, or debris formed during puncturing a tube cap in the measurement. This situation is called a pore blocking event, which may reduce reliability of the analyzer measurement. Conventional measurement time sequence of a blood cell analyzer is shown in FIG. 1. Firstly, a first sample and diluents are added to a reaction cell where the first sample is diluted and incubated; secondly, a certain amount of the mixture is taken from the reaction cell and injected into a counting cell where the mixture is measured by impedance method. At the same time the reaction cell is drained empty for a second sample; thirdly, the second sample and diluents are added into the reaction cell for second dilution and incubation. If a pore blocking event occurs when the first sample is measured using impedance method, conventional processing mode is that the first sample is placed again at the test location manually or by test tube rack retreat mechanism for another acquisition operation. And then, the first sample and the diluents are added again to the reaction cell for dilution and incubation, after that, a certain amount of the mixture is taken from the reaction cell and injected into the counting cell where the mixture is measured again by impedance method. A probability of failing to output test result is denoted as pore blocking probability. Conventional process of handling pore blocking events can be complex so that more blood samples may be needed. Moreover, the control process will be more complicated if a pore blocking event occurs in an analyzer with a continuous blood samples feeding system. So how to reduce pore blocking probability needs to be considered in developing a blood cell analyzer.

The present disclosure provides particle analyzers and particle test control methods and devices thereof, which are used to reduce probability of pore blocking.

The present disclosure is further illustrated by below embodiments and drawings thereof.

In one embodiment of the present disclosure, the test information of particles counting process is monitored in real time. When a pore blocking event occurs, a handling process may include suspending the sample test, performing an unblocking operation immediately, and then carrying out a second test using the remaining sample dilution. The handling process may avoid failure to output test result because a pore blocking event occurs in the first test, and the sample does not need to be placed again at the test location to do acquisition and dilution again, so as to reduce probability of pore blocking.

Full utilization of the residual diluted sample of the sample dilution can be achieved by not discharging the residual sample dilution after some of the diluted sample is extracted from a reaction cell. The residual sample dilution can be discharged after the test result is obtained. If a pore blocking event occurs during a first test, the residual diluted sample can be extracted from the reaction cell for a second test after unblocking operation. Fully utilization of the residual diluted sample of the sample dilution also can be achieved by using residual diluted sample kept in a tube between the reaction cell and a counting cell.

In following embodiments, a blood cell analyzer is an example of a particle analyzer for detailed description.

Figure 2:
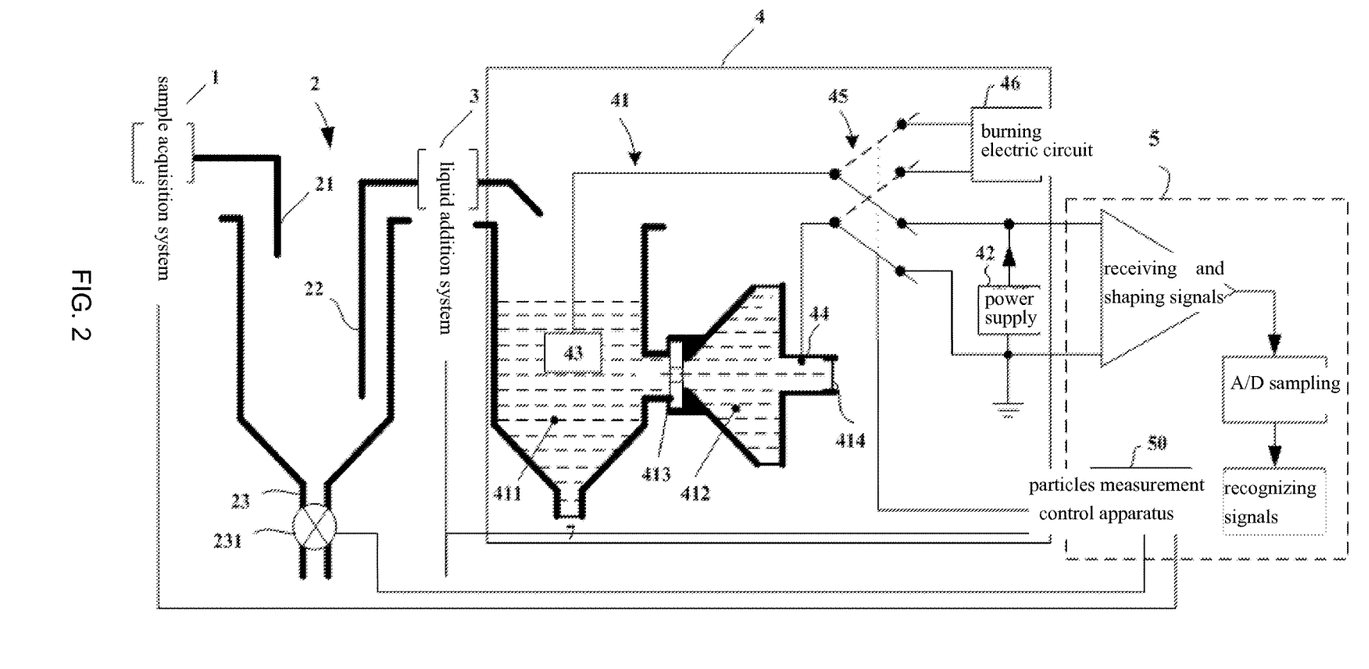
FIG. 2 is a block diagram which shows a blood cell analyzer in accordance with an embodiment of the present disclosure.

Referring to FIG. 2, a blood cell analyzer may include a reaction cell 2, a liquid addition system 3, a counting system 4 and a signal processing and control apparatus 5. A sample acquisition system 1 acquires a certain amount of sample in a test location, and injects it into the reaction cell 2. The sample is diluted by diluents in the reaction cell 2, or the sample may be diluted in multiple stages to obtain a diluted sample with a satisfactory dilution ratio. The counting system 4 may include a counting cell 41. The diluted sample in the reaction cell 2 is acquired and injected to the counting cell 41 by the liquid addition system 3. The counting system 4 counts the sample in the counting cell 41 and outputs a pore voltage.

In the embodiment, the reaction 2 may include a liquid inlet tube 21, a liquid outlet tube 22 and a liquid discharge tube 23. The liquid inlet tube 21 may connect to the sample acquisition system 1, the liquid outlet tube 22 may connect to the liquid addition system 3, and the liquid discharge tube 23 has a liquid discharge valve 231 which can switch between open and close status based on a control signal.

The counting system 4 may include a counting cell 41, a power supply 42, an anode electrode 43, and a cathode electrode 44. The counting cell 41 may include a front cell 411, a back cell 412 and a pore 413 which may locate between the front cell 411 and the back cell 412. When a sample is counted, there is electrolytic solution in the front cell 411 and back cell 412. One end of the anode electrode 43 is in the front cell 411 and one end of the cathode electrode 44 is in the back cell 412. The other ends of the anode electrode 43 and the cathode electrode 44 are connected to an output end of the power supply 42. The power supply 42 is usually a source having constant current. The back cell 412 further has a liquid outlet 414 which may be connected to a negative pressure chamber.

Figure 3:
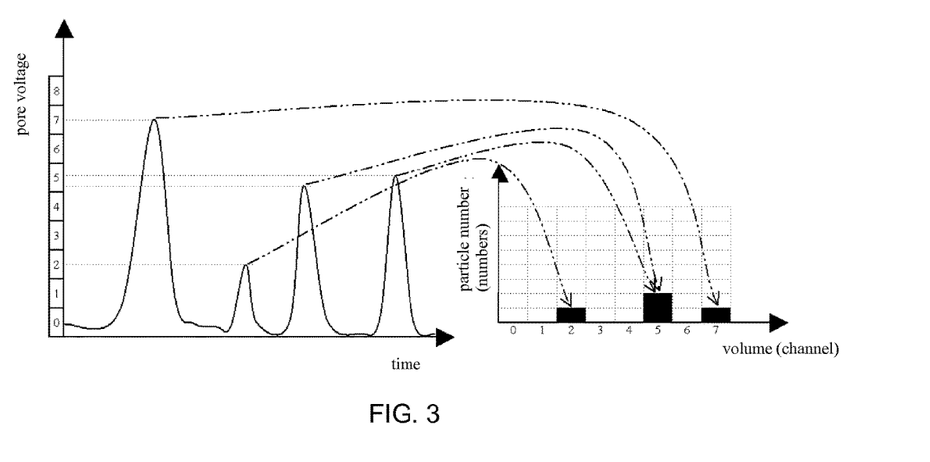
FIG. 3 is a diagram which shows how to recognize and count particles.

As shown in FIG. 3, the signal processing and control apparatus 5 may receive the pore voltage, and then shape and recognize voltage signals to obtain recognition and counting result. The result could be outputted by a printer or a display for examination by an operator. The result also could be stored for further examination.

In the embodiment, the working process of the blood analyzer may include following steps.

Figure 4A:
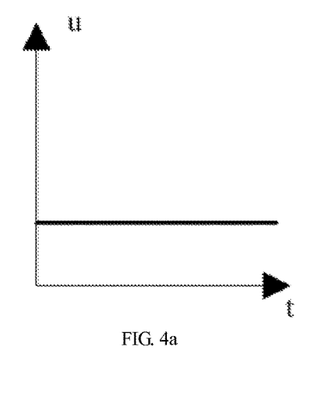
FIG. 4a is a diagram which shows a stable electric field formed by a source having constant current.
Figure 4B:
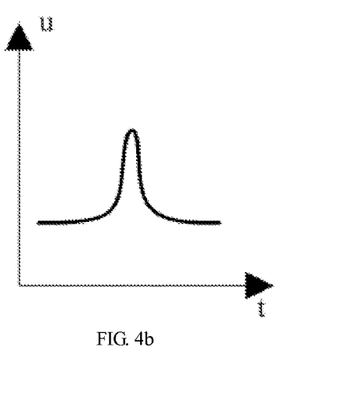
FIG. 4b is a diagram which shows a pulse signal that is formed when a blood cell passes through a pore.
Figure 4C:
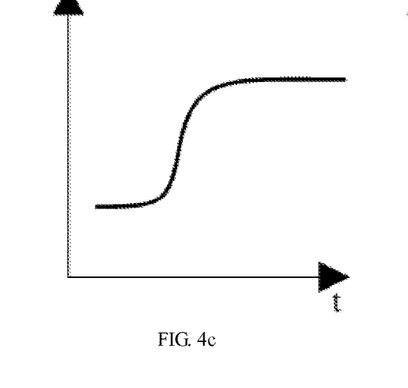
FIG. 4c is a diagram which shows that a pore voltage rises when a pore blocking event occurs.
Figure 4D:
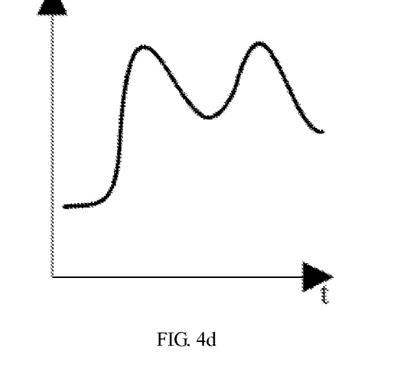
FIG. 4d is a diagram which shows a pore voltage fluctuates abnormally when a pore blocking event occurs.

The analyzer may take a certain amount of blood sample from a coagulation vacuum tube. The sample maybe mixed with a certain amount of diluents in a reaction cell to get the diluted sample with a fixed dilution ratio. Then, a certain amount of the diluted sample maybe acquired from the reaction cell and injected into a counting cell for counting by impedance method and obtaining counting results. The diluted sample maybe further mixed with a certain amount of reagent to get a second diluted sample when it is injected into the front cell 411. Driven by negative pressure, the second diluted sample may flow from the front cell 411 to the back cell 412 through the pore 413. During counting process, the sample may flow from the front cell 411 to the back cell 412. At the same time a stable electric current may be form. As shown in FIG. 4a, the source having constant current may be used between the anode electrode 43 and the cathode electrode 44 to form a stable electric current. As shown in FIG. 4b, when a cell passes through the pore, a pulse signal will be formed. As shown as FIGS. 4c and 4d, the pore voltage may rise or abnormally fluctuate if there is a foreign matter may block the pore.

Therefore, in the embodiment, the signal processing and control apparatus 5 maybe further control the liquid discharge valve 231 of the reaction cell 2 to be close status so as to maintain a residual diluted sample in the reaction cell 2 after the liquid addition system 3 acquires the diluted sample from the reaction cell 2 and injects the acquired diluted sample into the counting cell 41. And the apparatus 5 also may monitor a pore blocking event during counting process based on a pore voltage. If a pore blocking event occurs, a next test will be suspended and an unblocking operation will be performed. When unblocking operation is finished, the liquid addition system 3 acquires diluted sample again from the reaction cell 2 and inject the acquired diluted sample into the counting cell 41, then the sample in the counting cell will be re-counted by the impedance method.

Figure 5A:
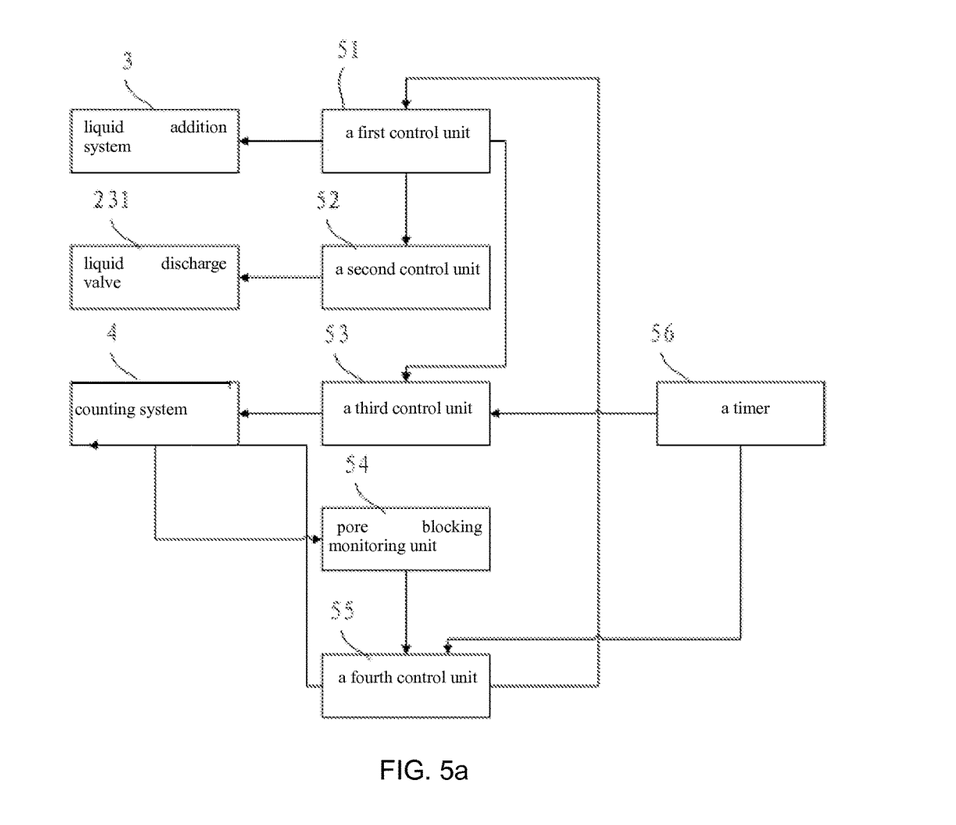
FIG. 5a is a block diagram which shows a particle test control device in accordance with one embodiment of the present disclosure.

In another embodiment, the signal processing and control apparatus 5 may include particles measurement control apparatus 50. As shown in FIG. 5a, the particles measurement control apparatus 50 may include a first control unit 51, a second control unit 52, a third control unit 53, a pore blocking monitoring unit 54 and a fourth control unit 55. The first control unit 51 is used to control the liquid addition system 3 to acquire a diluted sample from a reaction cell and inject the acquired diluted sample into a counting cell. The second control unit 52 may couple to the first control unit 51, which is used to control the liquid discharge valve 231 still to be a close status so as to keep a residual diluted sample in the reaction cell after the liquid addition system acquires diluted sample from the reaction cell. The third control unit 53 may couple to the first control unit 51, which is also called data acquisition control unit and used to control the counting system 4 to count the sample after the sample is injected into the counting cell. The pore blocking monitoring unit 54 may used to receive the pore voltage during the counting, determine whether pore blocking occurs and report the pore blocking event if the pore blocking occurs. The fourth control unit 55 may couple to the pore blocking monitoring unit 54, which is used to suspend a test based on the pore blocking event, perform unblocking operation, and output a control signal to the first control unit 51. The first control unit 51 may control the liquid addition system to acquire the sample again from the reaction cell and control the second control unit 52 to output a discharging control signal, and the liquid discharge valve of the reaction cell maybe be switched to an open status for discharging residual the diluted sample in the reaction cell.

Figure 5B:
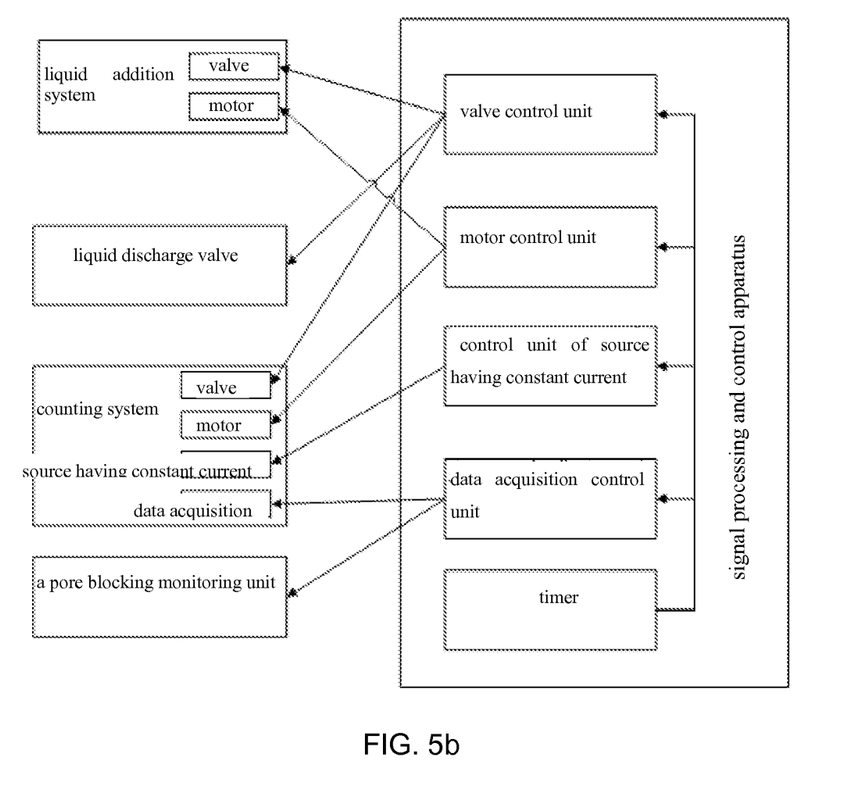
FIG. 5b is a block diagram which shows a particle test control device in accordance with another embodiment of the present disclosure.

As shown in FIG. 5b, in still another embodiment, the first control unit 51 maybe a motor control unit, which may control a motor of the liquid addition system 3 to acquire the diluted sample from the reaction cell and inject the acquired diluted sample into the counting cell. The motor control unit also may control other motors of the blood cell analyzer, such as motors of the counting system by impedance method, according to control commands. The second control unit 52 maybe a valve control unit, which is used to control the close or open status of the liquid discharge valve 231. The valve control unit also may be used to control other valves of the blood cell analyzer, such as valves of the counting system or valves of the liquid addition system 3, based on control commands.

In yet another embodiment, the particles measurement control apparatus 50 may include a timer 56, which may couple to the third control 53 and the fourth control 55. The third control unit 53 may control the timer 56 to start timing once the sample in the counting cell is to be counted. The timer 56 may output a time signal to the fourth control unit 55 when a predetermined period is reached. If the fourth control unit 55 receives a pore blocking event in the predetermined period, a test may be suspended and an unblocking operation may be performed. When the unblocking operation finishes, the fourth control unit 55 may output a control signal to the first control unit 51, the latter may control the liquid addition system 3 to acquire again the sample from the reaction cell and inject the acquired diluted sample into the counting cell. If the fourth control unit 55 does not receive a pore blocking event in the predetermined period, it may control the second control unit 52 to output a discharging signal. The liquid discharge valve 231 of the reaction cell may be switched to an open status, so that the residual diluted sample in the reaction cell may be discharged.

The timer may be integrated in the signal processing and control apparatus, or integrated the particles measurement control apparatus. Alternatively, the timer may be put apart from the signal processing and control apparatus as an independent element.

Figure 6:
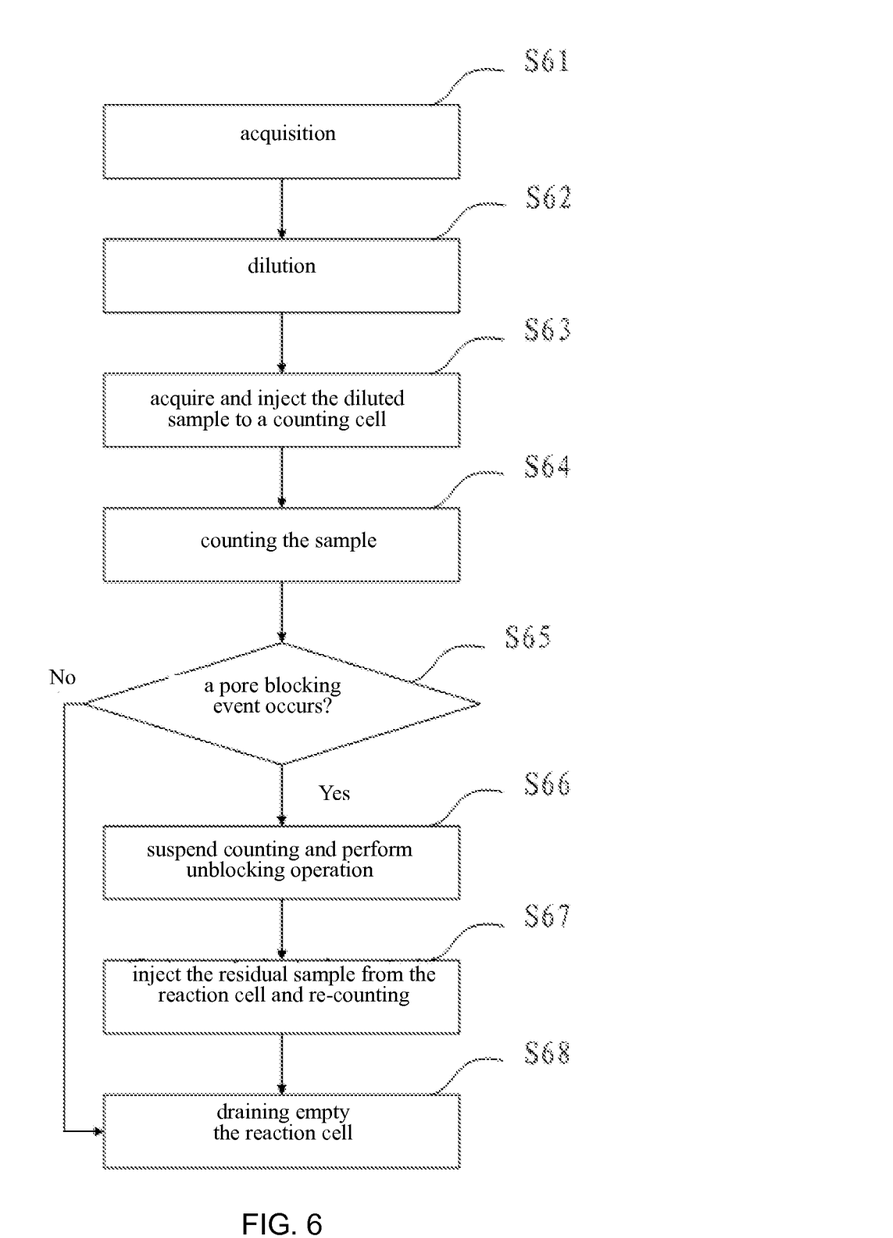
FIG. 6 is a flowchart of a particle test in accordance with one embodiment of the present disclosure.

As shown in FIG. 6, referring to the above blood cell analyzer, a particle measurement method in accordance with one embodiment may include following steps.

Step S61, controlling a sample acquisition system to acquire a sample in a test location.

Step S62, injecting the sample into a reaction cell to obtain a diluted sample.

Step S63, controlling a liquid addition system to acquire the diluted sample from the reaction cell, inject the acquired diluted sample into a counting cell, and keeping a liquid discharge valve of the reaction cell in a close status to maintain a residual diluted sample in the reaction cell.

Step S64, counting the sample in the counting cell by impedance method, and performing step S65 during the counting.

Step S65, monitoring and determining whether a pore blocking event occurs. If a pore blocking event occurs, performing step S66 otherwise performing Step S68. In one embodiment, when pore blocking is monitored and decided during a predetermined period beginning at counting by impedance method, a pore blocking event will be outputted. The predetermined period may be a period T, in which all of the acquired sample passes through the pore, or may be a period which is less than the period T. The predetermined period may be determined according to an analyzer's performance or computational algorithm for signal extraction and recognition. The predetermined period is not specially limited as long as collected signals during the period could obtain accurate counting and classification result. For example, if the time period of all of dilution sample through a pore is T, the predetermined period may be T/2.

Figure 7:
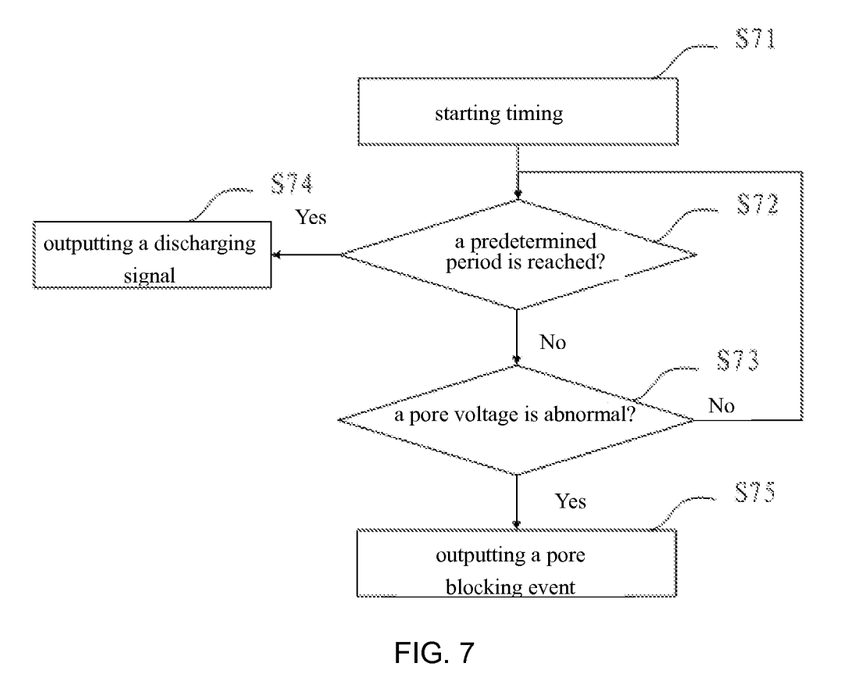
FIG. 7 is a flowchart of monitoring pore blocking in accordance with one embodiment of the present disclosure.

As shown in FIG. 7, in another embodiment, the pore blocking monitoring during the predetermined period may include following steps.

Step S71, starting timing once starting measurement by impedance method.

Step S72, determining whether a predetermined period is reached, if the predetermined period is reached, performing step S74 where a discharging signal is outputted, otherwise performing step S73 where a received pore voltage is determined instantly.

Step S73, instantly determining a received pore voltage in real time during the counting, if the pore voltage is abnormal, performing step S75 which includes outputting a pore blocking event, otherwise performing step S72.

Step S66, suspending a sample test which includes current and next test and performing an unblocking operation when pore blocking occurs.

Step S67, controlling the liquid addition system acquire sample again from the reaction cell and inject the acquired diluted sample into the counting cell, and re-counting the sample in the counting cell by impedance method. After acquiring the sample again from the reaction cell, performing step S68 which includes outputting a discharging control signal. Alternatively, keeping monitoring pore blocking during re-counting process, performing step S68 when the test finishes successfully.

Step S68, controlling the liquid discharge valve to an open status for discharging the residual diluted sample in the reaction cell.

There are several methods for determining whether pore blocking occurs according to real-time pore voltage. For example, base on at least one of the intensity of the real-time pore voltage, baseline voltage and pulse form, it may be determined whether pore voltage is abnormal or not. The abnormal pore voltage occurs may mean that pore blocking occurs.

In one embodiment, judging whether pore blocking occurs according to the intensity of the real-time pore voltage may include:

comparing the intensity of the pore voltage with a first threshold value;

recording a time duration when the intensity exceeds the first threshold value;

comparing the time duration with a second threshold value;

identifying a pore blocking event when the time duration exceeds the second threshold value.

In one embodiment, determining whether pore blocking occurs according to the baseline voltage of the real-time pore voltage may include:

calculating the baseline voltage of the pore voltage;

comparing the baseline voltage with a third threshold value;

identifying a pore blocking event when the baseline voltage exceeds the third threshold value.

Figure 8:
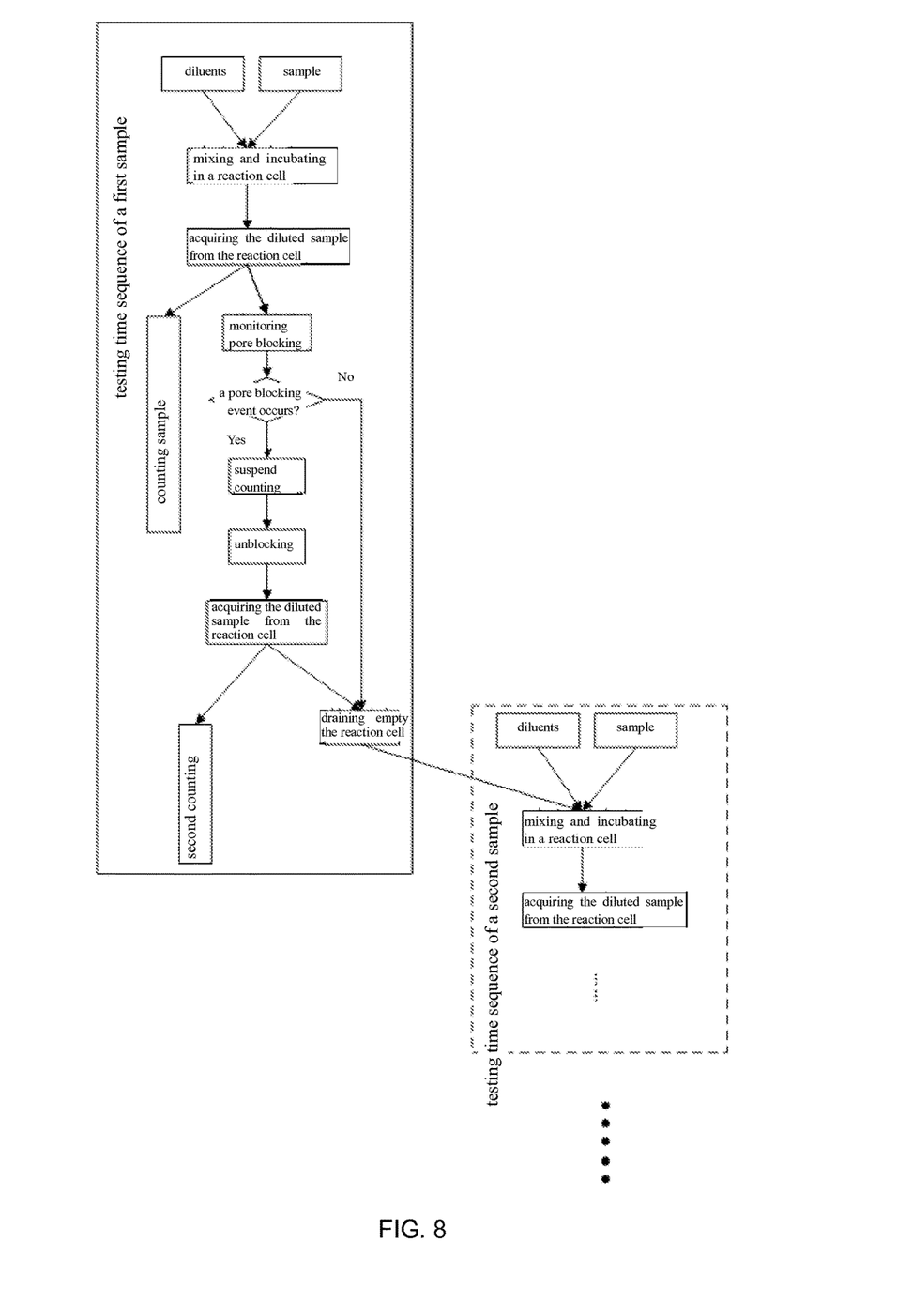
FIG. 8 is a test time sequence diagram of a blood cell analyzer in accordance with one embodiment of the present disclosure.

As shown in FIG. 8, sample testing time sequence may include:

A certain amount of reagent and a first sample are respectively injected into a reaction cell for mixing, incubating and obtaining a diluted sample with a satisfactory dilution ratio. A certain amount of the diluted sample is acquired from the reaction cell and injected into a counting cell for counting process. After some diluted sample is taken away, the reaction cell does not been discharged. A liquid discharge valve is kept in a close status to make a residual diluted sample to be stored in the reaction cell for a possible second counting process once a pore blocking event occurs. Pore blocking is monitored for a predetermined period during the counting process. If the pore blocking event occurs, some sample will be again acquired from the residual diluted sample in the reaction cell for a second counting after unblocking. If the pore blocking event does not occur in the predetermined period, or second acquisition finishes, the liquid discharge valve will be switched to an open status for discharging the reaction cell. The discharged reaction cell may be washed for testing another blood sample and a certain amount of reagent and the second blood sample are respectively injected into a reaction cell for mixing and incubating.

In the above embodiments, there is no need to find out the sample tube whose sample has a pore blocking event, place it again in the test location, acquire and dilute the sample again, because the residual diluted sample in the reaction cell could be acquired again for a second counting process when the pore blocking occurs. So the probability of pore blocking may be reduced. Moreover, the amount blood sample could be reduced, and requirement for minimum blood drawing amount to a tested person also could be reduce, because there is no need to acquire the blood sample twice.

Figure 9:
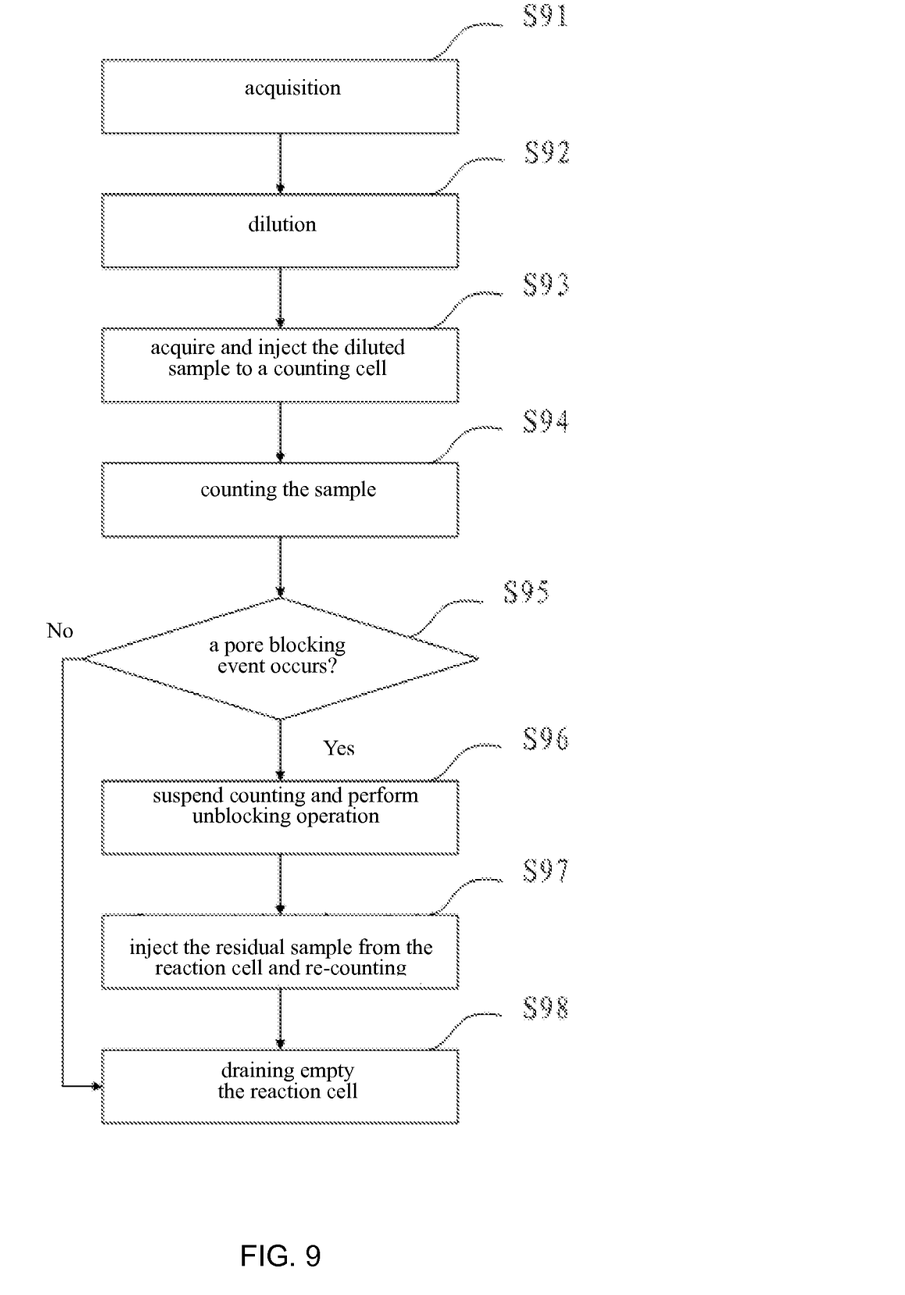
FIG. 9 is a flowchart of a particle test in accordance with another embodiment of the present disclosure.

Based on the above analyzer, in another embodiment, the blood cell analyzer may have a plurality of reaction cells for multiage dilution. As shown in FIG. 9, the analyzer's test process may include following steps.

Step S91, controlling a sample acquisition system to acquire a sample in a test location.

Step S92, injecting the sample into a plurality of reaction cells to perform multistage dilution, until a diluted sample having the satisfactory dilution ratio is obtained in the last reaction cell. In this embodiment, the sample dilution may not be finished in one reaction cell but in a plurality of reaction cells for multiage dilution. A certain amount of reagent and sample are respectively injected into a first reaction cell for a first level mixing and incubation, and then a certain amount of first level diluted sample is acquired from the first reaction cell and mixed with a certain amount of reagent in a second reaction cell for a second level mixing and incubation. These processes may be repeated several times until a diluted sample having the satisfactory dilution ratio is formed in the last reaction cell.

Step S93, controlling the liquid addition system to acquire the diluted sample from the last reaction cell and inject the acquired diluted sample into a counting cell, and keeping a liquid discharge valve of at least one of the reaction cells in a close status to maintain remainder diluted sample in at least one of the reaction cells. The liquid discharge valve of the last reaction cell may be kept in a close status for storing a remainder the last level diluted sample in the last reaction. Alternatively, the liquid discharge valve of the intermediate reaction cell may be kept in a close status for storing a remainder the intermediate level diluted sample in the reaction.

Step S94, counting the sample in the counting cell by impedance method.

Step S95, monitoring whether a pore blocking event occurs during the counting. The methods for determining a pore blocking event are as the same as that of above embodiments.

Step S96, suspending a sample test and performing an unblocking operation when a pore blocking event occurs.

Step S97, obtaining the diluted sample having the satisfactory dilution ratio from a reaction cell having residual diluted sample. If it is the last reaction cell that keeps the remainder in step S93, the diluted sample may be acquired from the last reaction cell, which may have the satisfactory dilution ratio and may not need to be diluted. If it is other reaction cell that keeps the remainder of intermediate level diluted sample in step S93, the diluted sample may be acquired from the reaction cell, which may not have the satisfactory dilution ratio and may need to be diluted until a diluted sample having the satisfactory dilution ratio is obtained. The diluted sample having the satisfactory dilution ratio may be injected into a counting cell, and counting again by impedance method.

Step S98, discharging all reaction cells.

A skilled artisan will understand that the example illustrations of apparatus or steps in above embodiments may also be used in this embodiment, such as step S67, step S72 or methods for determining whether pore blocking occurs.

Figure 10:
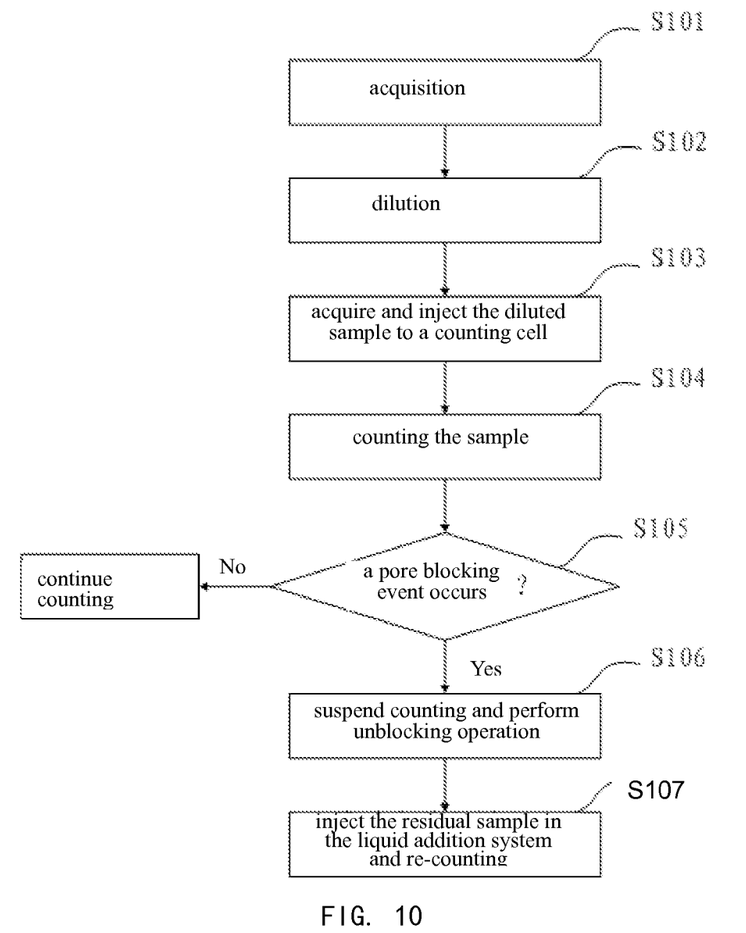
FIG. 10 is a flowchart of a particle test in accordance with still another embodiment of the present disclosure.

Based on the above analyzer, in still another embodiment, a liquid addition system of the blood cell analyzer may have longer tube. As shown in FIG. 10, the analyzer's test process may include following steps.

Step S101, controlling a sample acquisition system to acquire a sample in a test location.

Step S102, injecting the sample into a reaction cell to obtain a diluted sample.

Step S103, controlling a liquid addition system to acquire the diluted sample from the reaction cell, inject part of the diluted sample to a counting cell and keep a residual diluted sample in the liquid addition system. For example, the tube of the liquid addition system may be long enough to keep the diluted sample. Alternatively, the liquid addition system may have extra control valves. The control valves, which are installed at two ends of the tube, may be switched to a close status so as to keep the remainder the diluted sample in the tube after a diluted sample for a first counting is injected into a counting cell. When it is necessary to perform a second counting, the valves of tube may be switched to an open status, and the remainder diluted sample kept in the tube may be injected into a counting cell again. Alternatively, the valve may be installed at one end of the liquid addition system, which is near to the counting cell. The valve may be closed for keeping the remainder the diluted sample in the tube after a diluted sample for a first counting is injected into a counting cell. When it is necessary to perform a second counting, the valves of tube may be switched to an open status, and the remainder diluted sample kept in the tube may be injected into a counting cell again. Or, a syringe or an air pressure apparatus may be connected to the liquid addition system. The syringe or the air pressure apparatus may be used to control the diluted sample keeping in the tube of the liquid addition system or to be injected into the counting cell.

Step S104, counting the sample in the counting cell by impedance method, and monitoring whether a pore blocking event occurs during the counting. The methods for determining a pore blocking event are as the same as that of above embodiments.

Step S105, suspending the counting and performing an unblocking operation when a pore blocking event occurs.

Step S106, controlling the liquid addition system to inject the residual diluted sample into the counting cell after the unblocking operation, and re-counting the sample in the counting cell by impedance method.

In this embodiment, there is no need to consider when the reaction cell should be discharged. The reaction cell may be discharged once acquiring diluted sample at the first time or sometime after the first acquisition.

A skilled artisan will understand that the example illustrations of apparatus or steps in above embodiments may also be used in this embodiment, such as step S67, step S72 or methods for determining whether pore blocking occurs.

In above embodiments, an unblocking operation may preformed by one or more of following methods.

1. Backswing. In this method, liquid in the back cell is pushed to the front cell in a relatively high speed, so as to move away the foreign matter blocking the pore.
2. Burning. In the method, a relatively high electric current is set between the anode electrode and the cathode electrode. As shown in FIG. 2, particles measurement control apparatus 50 may control a changeover switch 45 switch from the power supply 42 to a burning electric circuit 46. The pore and area near it may be hot or even liquid near the pore may be boiled, so that the foreign matter blocking the pore may be destroyed.

In above embodiments, voltage in both sides of the pore element may be instantly monitored during counting process. When voltage in both sides of the pore element (i.e. pore voltage) rises or fluctuates abnormally, it may be identified that a pore blocking event occurs. Once the pore blocking occurs, sample counting may be suspended, an unblocking operation may be performed immediately after some necessary movements. And then, some sample may be acquired again from residual first diluted sample and re-counted. After that, the analyzer may automatically start a next blood sample test when the analyzer is in continuous sample injection mode.

Besides the blood cell analyzer described above, particles analyzer may be a workstation, urine analyzer, or other body fluid analyzer.

Although the present disclosure has been illustrated by way of the above embodiments and particular examples thereof, it will be appreciated by those skilled in the art that various changes, alterations and modifications may be made to the present disclosure without departing from the spirit and scope of the present disclosure as claimed.

The invention claimed is:

1. A particle test control method of particle analyzer, said method comprising:
    controlling a sample acquisition system to acquire a sample in a test location;
    injecting the acquired sample into a reaction cell to obtain a diluted sample;
    controlling a liquid addition system to acquire the diluted sample from a reaction cell and inject the acquired diluted sample into a counting cell, and keeping a liquid discharge valve of the reaction cell in a close status to maintain a residual diluted sample in the reaction cell;
    counting the sample in the counting cell by impedance method, and monitoring whether a pore blocking event occurs during counting;
    suspending counting and performing an unblocking operation if a pore blocking event occurs, wherein the unblocking operation comprises setting an anode electrode and a cathode electrode separately in the reaction cell and the counting cell, and supplying an electric current between the anode electrode and the cathode electrode to burn foreign matter blocking a pore; and
    controlling the liquid addition system to acquire the diluted sample again from the reaction cell and inject the acquired diluted sample into the counting cell after the unblocking operation, and re-counting the sample in the counting cell by impedance method.

2. The method according to claim 1, said method further comprising: outputting a discharge control signal after the liquid addition system acquires the diluted sample again from the reaction cell; controlling the liquid discharge valve to be in an open status for discharging the residual diluted sample in the reaction cell.

3. The method according to claim 1, said method further comprising:
    monitoring the pore blocking event during a predetermined period from the beginning of the counting by impedance method; and
    outputting the pore blocking event when the pore blocking event is identified.

4. The method according to claim 1, said method further comprising:
    outputting a discharge control signal when no pore blocking event occurs; and
    controlling the liquid discharge valve to be an open status for discharging the residual diluted sample in the reaction cell.

5. The method according to claim 1, said monitoring whether a pore blocking event occurs comprising:
    starting timing once starting measurement by impedance method;
    instantly determining a received pore voltage in real time during the timing;
    outputting the pore blocking event when determining the pore voltage is abnormal;
    determining whether a predetermined period is reached, outputting a discharge control signal when the predetermined period is reached, otherwise continuing determining the received pore voltage in real time.

6. The method according to claim 5, said determining a received pore voltage in real time comprising:
    determining whether the pore voltage is abnormal according to at least one of intensity of the real-time pore voltage, baseline voltage and pulse form.

7. A particle analyzer, said analyzer comprising:
    a reaction cell, where a sample is diluted, said reaction cell comprising an anode electrode, a liquid inlet tube, a liquid outlet tube and a liquid discharging tube, said liquid discharging tube having a liquid discharge valve which switches between a close status and an open status based on a control signal;
    a counting system, which comprises a counting cell, said counting system counting the sample injected into the counting cell and outputting a pore voltage; a liquid addition system, which acquires the diluted sample from the reaction cell and injects the acquired diluted sample into the counting cell;
    a signal processing and control apparatus, which acquires the pore voltage, and shapes and recognizes signals;
    is configured to control the liquid discharge valve of the reaction cell to be in the close status so as to maintain a residual diluted sample in the reaction cell after the liquid addition system acquires the diluted sample from the reaction cell and injects the acquired diluted sample into the counting cell;
    monitors pore blocking based on the pore voltage during the counting, suspends a next sample test and performs an unblocking operation when the pore blocking occurs, wherein the unblocking operation comprises supplying an electric current between the anode electrode and the cathode electrode to burn foreign matter blocking a pore; and
    controls the liquid addition system to acquire and inject the diluted sample to the counting cell again after the unblocking operation, and re-counts the sample in the counting cell by impedance method.

8. The analyzer according to claim 7, the signal processing and control apparatus further is configured to output a discharge control signal to the liquid discharge valve after the liquid addition system acquires the sample again from the reaction cell, control the liquid discharge valve to be in the open status for discharging reaction cell, control the liquid discharge valve to be an open status for discharging the residual diluted sample in the reaction cell.

9. The analyzer according to claim 7, said analyzer further comprising a timer, said timer connecting to the signal processing and control apparatus;
   said signal processing the control apparatus controlling said timer to start timing once the sample in the counting cell is counted by impedance method;
   said timer outputting a time signal to said signal processing and control apparatus when a predetermined period is reached;
   said signal processing and control apparatus is configured to suspend a test and perform the unblocking operation when the pore blocking event occurs in the predetermined period, and control the liquid addition system to acquire the sample again from the reaction cell and inject the acquired diluted sample into the counting cell for re-counting the sample in the counting cell by impedance method.

10. The analyzer according to claim 9, said signal processing and control apparatus is configured to output a discharge control signal when no pore blocking event occurs in the predetermined period, control the liquid discharge valve to be in the open status for discharging the residual diluted sample in the reaction cell.

11. The analyzer according to claim 9, said signal processing and control apparatus is configured to determine whether the pore blocking occurs according to at least one of intensity of the real-time pore voltage, baseline voltage and pulse form.

12. A method particle test control method of particle analyzer, said method comprising:
   controlling a sample acquisition system to acquire a sample in a test location;
   injecting the sample into a reaction cell to obtain a diluted sample;
   controlling a liquid addition system to acquire the diluted sample from the reaction cell, inject part of the diluted sample to a counting cell and keep a residual diluted sample in the liquid addition system;
   counting the sample in the counting cell by impedance method, and monitoring whether a pore blocking event occurs during counting;
   suspending a sample test and performing an unblocking operation when a pore blocking event occurs; and
   controlling the liquid addition system to inject the residual diluted sample into the counting cell after the unblocking operation, and re-counting the sample in the counting cell by impedance method.

13. The method according to claim 12, said method further controlling two control valves which are set at two ends of a tube of the liquid addition system in a close status after the liquid addition system acquiring the diluted sample from the reaction cell and injecting the acquired diluted sample into the counting cell; and controlling said control valves to be in the open status after the unblocking operation for injecting the residual diluted sample in the tube into the counting cell.

* * * * *